United States Patent [19]
Kambara et al.

[11] Patent Number: 5,817,464
[45] Date of Patent: *Oct. 6, 1998

[54] FRACTIONATION METHOD FOR NUCLEOTIDE FRAGMENTS

[75] Inventors: Hideki Kambara, Hachiouji; Kazunori Okano, Shiki; Chihiro Uematsu, Kokubunji, all of Japan

[73] Assignee: Hitachi, Ltd., Tokyo, Japan

[*] Notice: The term of this patent shall not extend beyond the expiration date of Pat. No. 5,650,274.

[21] Appl. No.: 748,900

[22] Filed: Nov. 15, 1996

Related U.S. Application Data

[63] Continuation of Ser. No. 321,624, Oct. 12, 1994, abandoned.

[30] Foreign Application Priority Data

Oct. 26, 1993 [JP] Japan .................................. 5-266936

[51] Int. Cl.$^6$ .............. C12Q 1/68; C12Q 1/70; C07H 21/04; C12P 19/34
[52] U.S. Cl. ................ 435/6; 435/6; 435/91.2; 536/23.1; 536/24.3
[58] Field of Search ............ 435/6, 91.2; 536/23.1, 536/24.3; 935/76, 77, 78

[56] References Cited

U.S. PATENT DOCUMENTS

| | | | |
|---|---|---|---|
| 4,962,020 | 10/1990 | Tabor et al. | 435/6 |
| 4,997,928 | 3/1991 | Hobbs | 536/27 |
| 5,064,754 | 11/1991 | Mills | 435/6 |
| 5,122,345 | 6/1992 | Tabor et al. | 422/116 |
| 5,124,247 | 6/1992 | Ansorge | 435/6 |
| 5,171,534 | 12/1992 | Smith et al. | 422/82.05 |
| 5,221,518 | 6/1993 | Mills | 422/62 |
| 5,308,751 | 5/1994 | Ohkawa et al. | 435/6 |
| 5,324,631 | 6/1994 | Helentjaris et al. | 435/6 |
| 5,409,811 | 4/1995 | Tabor et al. | 435/6 |
| 5,470,705 | 11/1995 | Grossman et al. | 435/6 |
| 5,514,543 | 5/1996 | Grossman et al. | 435/6 |
| 5,650,274 | 7/1997 | Kambara et al. | |

FOREIGN PATENT DOCUMENTS

WO 9325563  12/1993  WIPO .

OTHER PUBLICATIONS

Sanger et al. Proc. Natl. Acad. Sci. USA 74(12): pp. 5463–5467 (1977).
Rosenthal et al. Nucl. Acids Res. 18(10): pp. 3095–3096 (1990).

Chemical Abstracts, vol. 91, No. 23, Dec. 3, 1979. G.E. Sulimova "Methods for DNA fractionation", p. 263, No. 188 841f; & Fiz. –Khim. Metody Mol. Biol. 1978, 3–32.

Chemical Abstracts, vol. 87, No. 13, Sep. 26, 1977, G.G. Peters "The fractionation and characterization of the low molecular weight RNA of RNA tumor viruses", p. 287, No. 98 237b; & Immune RNA Neoplasia, (Proc. Symp.) 1975 (Pub. 1976), 13–25.

Chemical Abstracts, vol. 73, No. 13, Sep. 28, 1970, R.M. Kothari "present chromatographic methods of fractionating DNA", p. 44, No. 63 001d; & Chromatogr. Rev. 1970, 12(2), 127–55.

Patent Abstracts of Japan, unexamined applications, C. Section, vol. 16, No. 207. May 18, 1992, The Patent Office Japanese Government, p. 18 C 941; & JP–A–04 036 199 (Iatron).

Toneguzzo et al. Biotechniques 6(5):460–469 (1988).

Rosenthal et al. Nucleic Acids Research 19(19):5395–5401 (1991).

Espelund et al. Biotechniques 13(1):74–81 (1992).

*Primary Examiner*—W. Gary Jones
*Assistant Examiner*—Ethan Whisenant
*Attorney, Agent, or Firm*—Antonelli, Terry, Stout & Kraus, LLP

[57] ABSTRACT

A fractionation method for DNA fragments according to the present invention comprises a first step of preparing a probe chip or a set of probe chips immobilizing independently a DNA probe having a first sequence part having a specific known sequence part together with a part of enzyme recognition sequence and a second sequence part composed of a combination of one to six bases adjacent to the first sequence part at 3' terminus, a second step of introducing a DNA oligomer composed of a part of enzyme recognition sequence and a sequence complementary to the known sequence part into the fragment termini of DNA fragments from restriction enzyme cleavage, and a third step of placing the probe chip or the set of probe chips in a solution containing the nucleotide fragments with the introduced DNA oligomer produced at the second step, for at least hybridization and the complementary strand extension of the DNA probe, whereby the DNA fragments are fractionated.

34 Claims, 6 Drawing Sheets

FRACTIONATION METHOD FOR NUCLEOTIDE FRAGMENTS

This application is a continuation application of Ser. No. 08/321,624 filed Oct. 12, 1994, and now abandoned.

BACKGROUND OF THE INVENTION

The present invention relates to a fractionation method for nucleotide fragments (DNA or RNA) and a DNA sequencing method of the same.

When DNAs of different lengths are in a mixture, for example, in the state of enzyme cleaved products of a long DNA, it is impossible to immediately determine their DNA sequences. Conventionally, two methods are known as the method for analyzing such DNA sequences. A first method comprises separating individual DNA fragments by gel electrophoresis and subjecting the separated individual fragments to DNA sequencing. A second method comprises inserting these DNAs into an appropriate vector (cloning), injecting the vector into *E. coli* which is then cultured on agar medium, reculturing *E. coli* in each generated colony and extracting DNA from the bacterium in multiplication for DNA sequencing.

SUMMARY OF THE INVENTION

For gel electrophoresis to be used for DNA separation, an agarose gel or a polyacrylamide gel may be used. By gel electrophoresis, the difference of a single base in DNA of a length of 400 bases or less may be discriminated, and furthermore, DNA of a length of 300 bases or less may be separated and fractionated. However, as the length gets longer, the separation potency of the gel may be lowered. Therefore, the first conventional method has a disadvantage because individual DNA fragments cannot always be separated with identical fractionation results.

Alternatively, the second conventional method via cloning has a disadvantage because the method demands laborious works; because a DNA fragment of a far shorter length cannot be cloned; and because a large number of clones should be sequenced for obtaining the complete DNA sequence because the total length of the sequenced fragments will be 5-10 times of the target DNA length for covering the complete DNA sequence without any non-sequenced island. The base reading redundancy is 5-10 on average.

A DNA fractionation method utilizing hybridization is known, comprising immobilizing DNA probes of various DNA sequences onto a solid surface and hybridizing objective DNA fragments with the probes, whereby the fragments are separated and fractionated. However, it is necessary in this case that the sequences of the objective DNA fragments should be known to prepare the probes on a solid surface, so the method is not applicable for classifying and separating DNA fragments with unknown sequences.

The present invention overcomes these problems, and provides a method for readily separating DNA fragments with unknown sequences, an analytical method of DNA sequence and the like. In the specification, fractionation means collecting DNA fragments after separating them by the difference in terminal base sequences adjacent to the cutting site.

The present invention relates to a fractionation method for DNA fragments, comprising treating a mixture of DNA fragments having an introduced oligonucleotide of a known sequence at the terminus with a probe chip or a set of probe chips which have solid surface immobilized with various DNA probes having a sequence selecting part of an oligonucleotide of a length at which length the oligonucleotide cannot hybridize solely in a stable fashion, i.e. an oligonucleotide of one to six bases, at the 3' terminus adjacent to the specific known oligonucleotide sequence complementary to the known part of the above DNA fragments, and separating the mixed DNA fragments, at least through the process of hybridization and complementary DNA strand extension reaction. Stable hybridization of the probe with DNA screening is performed by using the introduced known DNA sequence, while the sequence selecting part of the probe is used for selecting a DNA fragment by the occurrence of the DNA complementary strand extension of the hybridized probe which stabilizes the hybrid. When the DNA complementary strand extension occurs to an oligonucleotide probe being hybridized with a DNA fragment perfectly, the hybridization force increases which can be used to separate the DNA fragment from other DNA fragments hybridized to oligonucleotide probes inperfectly; therefore, the DNA strand extension does not occur. By the separation method described above, DNA fragments completely hybridized with DNA probes can be separated and collected, if necessary.

Such probe chip includes, for example, a slender rod, wire, sheet, ribbon, etc., immobilized with DNA probes, or solid surface with positions (cells) individually immobilized with different types of DNA probes.

By the method, a single probe chip or a plurality of probe chips retaining DNA probes, are simultaneously placed in a solution containing DNA fragments, for DNA complementary strand extension reaction to generate double stranded DNA(s), which is (are) then collected separately.

According to the method, at least one repetition is made of a cycle of the process of DNA complementary strand extension reaction and a process comprising raising the temperature of a mixture of resulting the complementary strand extension reaction products to separate the non-extended DNA probe from the DNA fragment sample, while leaving the extended DNA probe hybridized to the DNA sample.

In the above method, when DNA complementary strand extension reaction is carried out, using probe chips where DNA probes are individually immobilized onto different solid surfaces or are individually immobilized onto different positions (cells) of a solid surface, together with a free oligonucleotide oligomer (primer), the number of DNA fragments can be amplified and separated on the solid surface by raising and then lowering the reaction temperature repeatedly, which is a kind of PCR (Polymerase Chain Reaction) with a solid surface. Here, the DNA probe immobilized onto the solid surface contains a common sequence and a sequence selecting part at 3' terminus, although the free primer contains only a common sequence.

The DNA fragments obtained by the fractionation method in accordance with the present invention are used for DNA sequencing, as they are or after individual separation and isolation.

The DNA sequencing method in accordance with the present invention can be applied to DNA sequencing of DNA fragments after collecting separately as described above or of DNA fragments after separation or isolation.

By attaching a known DNA oligomer to the terminus of a DNA fragment, the DNA fragment is modified into a form hybridizable to a DNA probe. A sequence selecting part of several bases attached to the 3' terminus of the DNA probe is arranged so as to select an objective DNA fragment. For the sequence of several bases at 3' terminus, all combinations of several bases should be prepared. DNA probes each having a sequence selecting part composed of a sequence from such combination and a known sequence complementary to the known oligomer introduced into a DNA fragment are attached individually to the tips of different slender rods. When one of the probe sequences at the 3' terminus completely matches the DNA fragment sequence adjacent to the cutting site, DNA complementary strand extension proceeds with the probes to increase the hybridization stability, so that DNA fragment-DNA probe pairs having mismatched sequences around the terminus can be discriminated from the matched pairs by raising the temperature.

As the sequence of the probe, adjacent to the several bases at 3' terminus for selecting DNA fragment, is common to all probes attached to slender rods, all DNA fragments hybridize to DNA probes. However, a great number of so-called mismatched pairs (a pair of DNA fragment and DNA probe), which are not attached to each other at 3' terminus, are present at a stage where DNA fragments and DNA probes are mixed to form hybridomers. The DNA complementary strand extension occurs only for the completely matched pairs. Thus, a DNA fragment hybridized to a probe without complementary strand extension is dehybridized and then rehybridized to another probe, while a DNA fragment hybridized to a probe extended by complementary strand extension reaction is left as it is. By repeating such procedure, the number of pairs (i.e. a pair of a DNA fragment and the DNA probe) having the DNA probe with DNA complementary strand extension can be increased. In such manner, matched pairs are isolated on the solid surfaces and are separated.

In accordance with the present invention, DNA fragments of unknown DNA sequences can be separated on the basis of the difference in their terminal sequences. The separated DNA fragments are fractionated and amplified by PCR for sequencing. Thus, DNA analysis can be done without conventional cloning process requiring much labor and a longer time. Also, the present invention is applicable in various fields, because any DNA libraries can be separated and isolated on the basis of the difference in their terminal sequences.

The present invention can be summarized as follows. Preparing a probe chip or probe chips immobilizing each DNA probe individually on a solid surface, the sequence of which has a specific known sequence part, a part of restriction enzyme recognition sequence (if necessary), (the combined sequence is a first sequence part) and a sequence selecting part of 1–6 bases at 3' terminus (a second sequence part) adjacent to the known sequence part, introducing the known sequence part into the fragment termini of a DNA fragment mixture from restriction enzyme cleavage, mixing the probe or probes with the mixture DNA fragments for hybridization, thereby extending DNA probes to produce the complementary strands, individual DNA fragments are separated by the difference in their terminal base sequences using the hybridization stability after the complementary strand extension reactions. The DNA fragments are used for sequencing as they are or after isolation and amplifications. DNA fragments with unknown DNA sequences can be separated on the basis of the difference in sequence around termini, whereby subcloning process can be neglected.

DESCRIPTION OF THE PREFERRED EMBODIMENTS

The present invention will now be explained in examples. The technical scope of the present invention is not limited to these examples, however.

Figure 1:
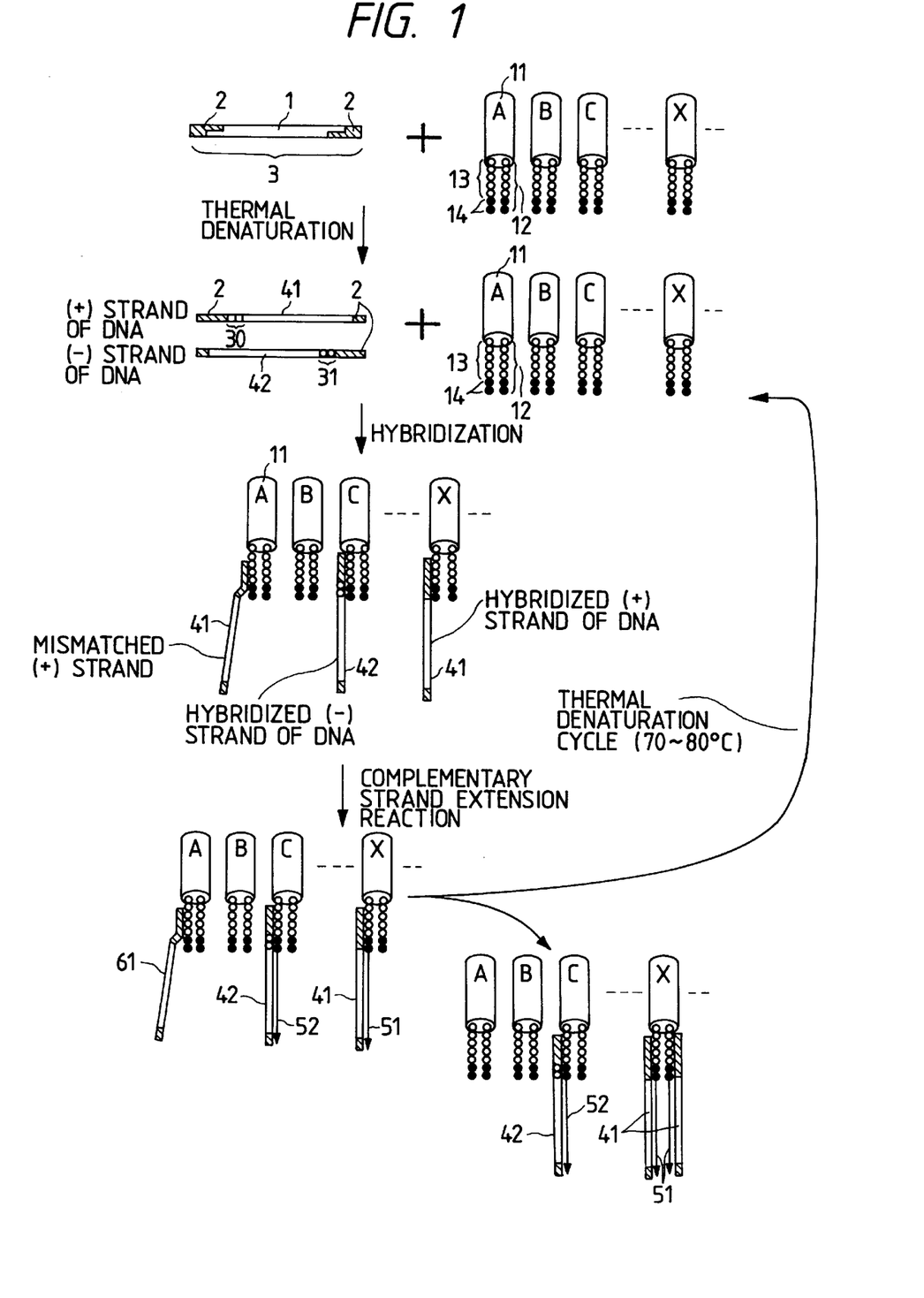
FIG. 1 is a schematic view of the DNA extraction in accordance with the present invention.
Figure 2:
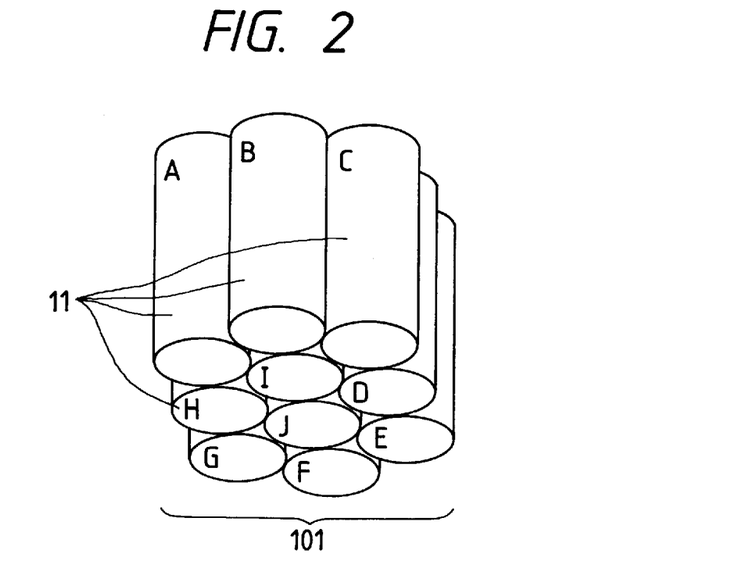
FIG. 2 is a schematic view of the DNA extracting slender rods in a bundle in accordance with the present invention.

With reference to FIGS. 1 and 2, the principle of the present invention will be explained in a simple example. Through ligation, firstly, DNA oligomer 2 having a known sequence is ligated to the terminus of double stranded DNA fragment 1 produced by restriction enzyme cleavage. Here, the part of ligated oligomer and the recognition sequence of enzyme is the known sequence part. Otherwise, poly A is attached to the terminus of single stranded DNA with terminal transferase, to introduce the known sequence into the terminus. In FIG. 1, explanation will now be made, by illustrating an example of sample fragment 3 with known sequence oligomer 2 introduced into the terminus of the double stranded DNA fragment 1.

DNA probe 12 is attached to the tip of slender tube or slender rod 11. The DNA probe 12 attached to the slender tube or slender rod 11 is composed of sequence selecting part 14 of several bases at 3' terminus and known sequence part 13. Herein, DNA probes 12 each having the sequence selecting part 14 having a different sequence from each other are individually attached to slender tube or slender rods 11, and in the example shown in FIG. 1, the sequence selecting part 14 is composed of two bases while the known sequence part 13 is composed of fifteen bases (one circle does not represent one base). The base length of the known sequence and the selective sequence is long enough to make stable hybridization with DNA fragments. The slender rod 11 is immersed in a sample solution containing sample fragment 3 and then the sample fragment 3 is denatured followed by annealing. The resulting objective DNA fragments 41, 42 are hybridized with the DNA probe 12 for DNA complementary strand extension. During this reaction, hybridized DNA probe 12 without mismatch at their 3' terminus may generate DNAs 51, 52 through complementary strand extension; otherwise, complementary strand extension may not proceed for DNA probes with mismatch at their terminus because mismatched DNA fragment 41 may generate hybridized DNA fragment 61.

So as to dehybridize the mismatched DNA fragment 61 from the probe, the temperature of the sample solution is raised to 70° to 85° C. Subsequently, the temperature is lowered to hybridize the objective DNA fragments 41, 42 with the DNA probe for complementary strand extension. After repeating such procedure, the solution is kept at a higher temperature and the slender rod 11 is drawn out at a higher temperature to collect the fragments hybridized with the extended probes, while leaving the mismatched DNA fragment in the solution. Then, the tip of each slender rod is transferred into a different bottle filled with a buffer solution, then the temperature of the rod is raised to dehybridize the DNA fragment from the probe on the tip. By bundling a plurality of slender rods (A, B, C, - - - ) of FIG. 1 as shown in FIG. 2 to make a set of slender rods 101 (A, B, C, - - - , I, J), the reaction process described above may progress simultaneously. Each slender rod tip is immersed in a buffer solution, and by raising the temperature, DNA fragments each having a matched 3' terminal DNA sequence with the DNA probe immobilized on the slender rod are fractionated. Using the fractionated DNA fragments, DNA sequence is determined.

(Example 1)

Hind III digestion products of λ-phage DNA were used as samples. Fragments from restriction enzyme cleavage are ligated to a fluorescence (sulforhodamine 101) labeled DNA oligomer via ligation reaction. Alternatively, a surface of a glass rod (a 0.2-mm diameter at the tip) is treated at a length from the tip to 5 mm below for attaching DNA probes having an amino residue at 5' terminus, thereby preparing a large number of glass rods each immobilized with the DNA probe at the tip thereof.

For immobilization, silanization reaction is used to introduce various activated residues onto the glass surface. For example, the glass surface is treated with dilute aqueous acetic acid solution of 3-glycidoxypropyltrimethoxysilane, and is then baked at 90° to 105° C. to introduce the epoxy group onto the glass surface. Then, reaction with a 5'-amino DNA probe at pH 9 generates a glass rod retaining the DNA probe on the glass surface thereof. Another method comprises introducing an amino residue onto the glass surface using 3-aminopropyltrimethoxysilane, 3-(2-aminoethylaminopropyl)trimethoxysilane, etc., and treating the surface with succinic anhydride, thereby introducing the carboxyl group into the amino residue. Subsequently, reaction with a 5'-amino DNA probe in the presence of water-soluble carbodiimide generates a glass rod retaining the DNA probe.

The DNA sequence of the DNA probe is composed of at least a common sequence part, which is a complementary sequence (which is the same as the sequence at 5' terminus) to the sequence at 3' terminus of the fluorescence labeled oligomer used for the ligation to the DNA fragments, a part of enzyme recognition sequence, and a sequence selecting part of an appropriate sequence of two bases at 3' terminus. The selectivity reaches highest when the terminal sequence selecting part is composed of one to two bases. The number of a combination of terminal two bases is 16, so 16 types of slender rods individually retaining 16 DNA probes are to be prepared. The 3'-terminal sequence selecting part may be composed of three to four bases, and in the case of three bases, 64 types of such slender rods should be prepared. For four bases, 256 types of such rods should be prepared. When the length of a terminal sequence selecting part is longer, complementary strand extension may sometimes occur even if the base matching between probe DNA and sample DNA is insufficient. So as to prevent such extension occurring for mismatched pairs, terminal hybridization potential should be distinctively decreased to prevent a stable hybridomer formation among mismatched pairs at a terminal. When several bases in the common sequence part and especially bases adjacent to a sequence selecting part at 3' terminus is modified into inosine or is modified into a mismatched sequence, the stability of hybridization around the terminus then depends largely on the matching of the sequence selecting part, and thus, can be adjusted so that the complementary strand extension does not sufficiently proceed if even a single base is mismatched in the sequence selecting part. The length of the sequence selecting part may preferably be 6-mer or less which singly does not form a stable hybridized product, and is more preferably 1-mer to 3-mer because complementary strand extension is much affected by the degree of base matching at 3' terminus of 1-mer to 3-mer.

Then, a part of fluorescence labeled fragments produced by ligation is fractionated and analyzed by gel electrophoresis to generate a gel electrophoresis pattern of the fragments. When the number of the fragments appearing the electrophoresis patterns is more than ten in a single stranded form, the DNA species in a fraction is too more to analyze without separation. Therefore, DNA fragments are separated and fractionated again via gel electrophoresis. Finally, the number of fragments contained in a fraction should be 10 or less in a single strand form. This is because the number of DNA probe types to be used subsequently for DNA separation should be 16, so that the trapping of more than two DNA fragment species by a single probe species should be prevented.

In the case of Hind III digestion product of λ phage, the number of fragments is 14, but the fragments were used for sequencing without separation as a trial. Dissolving the DNA fragments in a buffer solution, 16 slender rods each immobilized with individual 16 types of DNA probes are immersed in the solution for hybridization. So as to promote hybridization, double stranded DNA may be thermally denatured or its 3' terminus may be modified into a single stranded form by exonuclease digestion at the 5' terminus of the double strand. Deoxynucleotide triphosphate (dNTP) as substrates for complementary strand extension are added together with DNA polymerase, to promote complementary strand extension. Because complementary strand extension proceeds for DNA probe with 3' terminus in completely matched hybridization with a DNA fragment, the hybridization strength of the DNA probe to the DNA fragment is increased. On the other hand, complementary strand extension does not occur on a DNA probe under a partially mismatched hybridization condition so such hybridization strength is weak.

From a statistical reason, only 1/16 of DNA fragments can hybridize to the probe without mismatch by the hybridization procedure comprising once immersing 16 slender rods in the solution and simultaneously immersing 16 types of DNA probe chips in a solution containing DNA fragments. After complementary strand extension terminates, thermal denaturation by elevating temperature up to 70° to 80° C. is carried out to promote dehybridization of DNA fragments from a probe. Then, the temperature is lowered to hybridize DNA fragments again to non-extended another probe for complementary strand extension. By repeating such procedure, the number of a DNA pair in complete matching can be increased. If repeating the cycle at a number larger than the number of the DNA probe types, an objective DNA fragment can be trapped almost completely with a matched DNA probe, which is then isolated. A smaller number of the DNA probe types to be simultaneously hybridized decreases the number of repetition of such procedure required for sufficient isolation. Thus, the use of a smaller number of probe species is a more, for example, the use of a single DNA probe chip, the use of a set of four to five probe chips, or the use of only necessary DNA probe chips after checking the necessity by investigation 2-base sequence adjacent to the common sequence part of DNA fragments, and the like.

Figure 3:
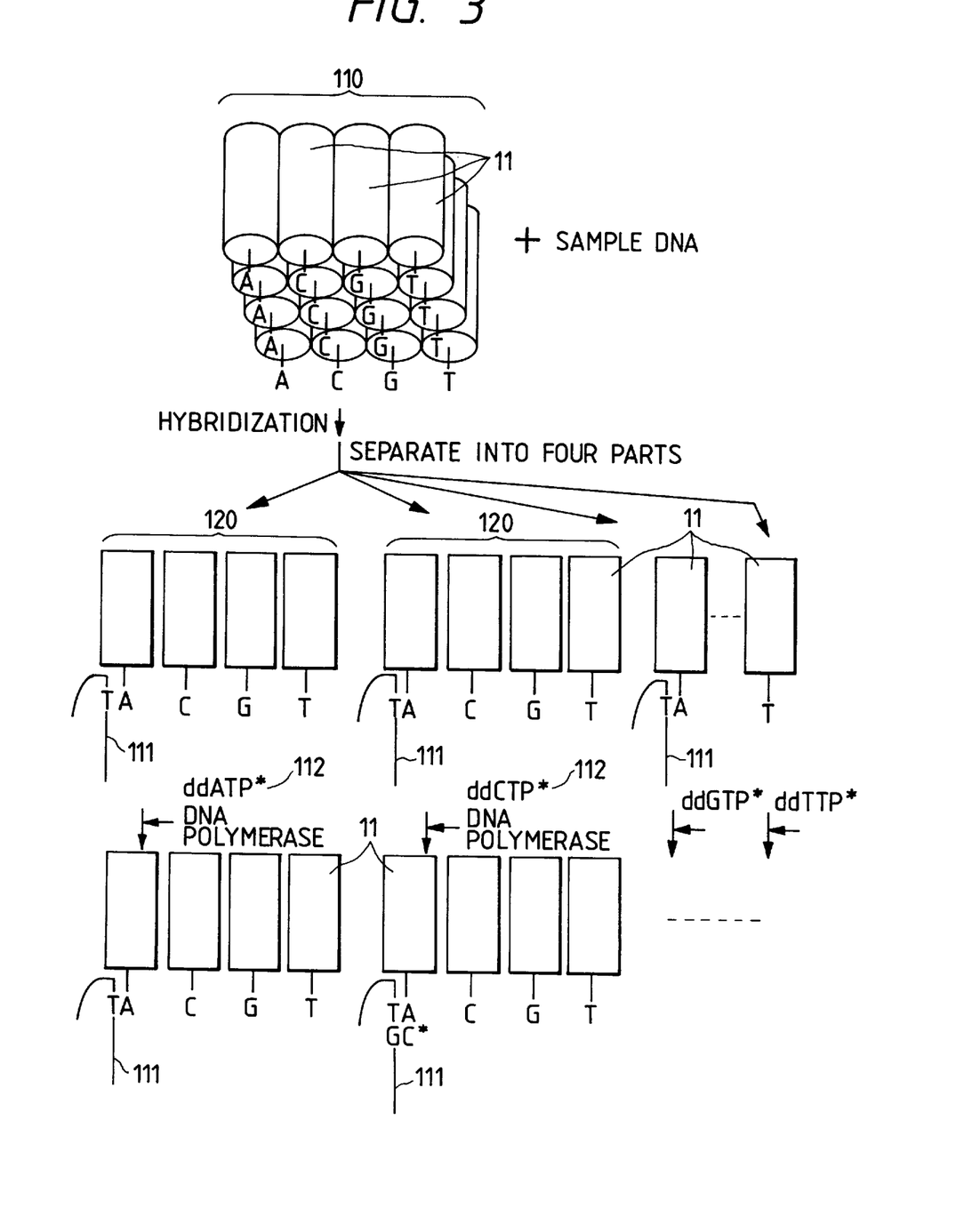
FIG. 3 is a view depicting the method for analyzing two bases at DNA fragment terminus.

So as to identify the 2-base sequence adjacent to the common sequence part introduced into the 3' terminus of DNA fragments, use is made of glass rod 11 immobilized with a DNA probe having A, C, G and T as the first base adjacent to the common sequence part, following the procedure shown in FIG. 3. Bundle 110 of 16 slender rods, each group of four rods having a set of A, C, G and T termini, is reacted for hybridization simultaneously with a sample mixture solution. After the hybridization reaction, the glass rods are washed in water to wash off the non-hybridized sample, and then, the bundle 110 is divided into four probe groups, each probe group having a set of A, C, G and T termini. As shown in FIG. 3, consequently, hybridized DNA 111 is captured onto the glass rods. Subsequently, by adding fluorescence labeled terminator 112 (dideoxynucleotide triphosphate; ddNTP*), ddNTP* is introduced as a second nucleotide adjacent to the common sequence part of the DNA probe, by DNA polymerase reaction (Symbol "*" represents fluorescence label).

Figure 4:
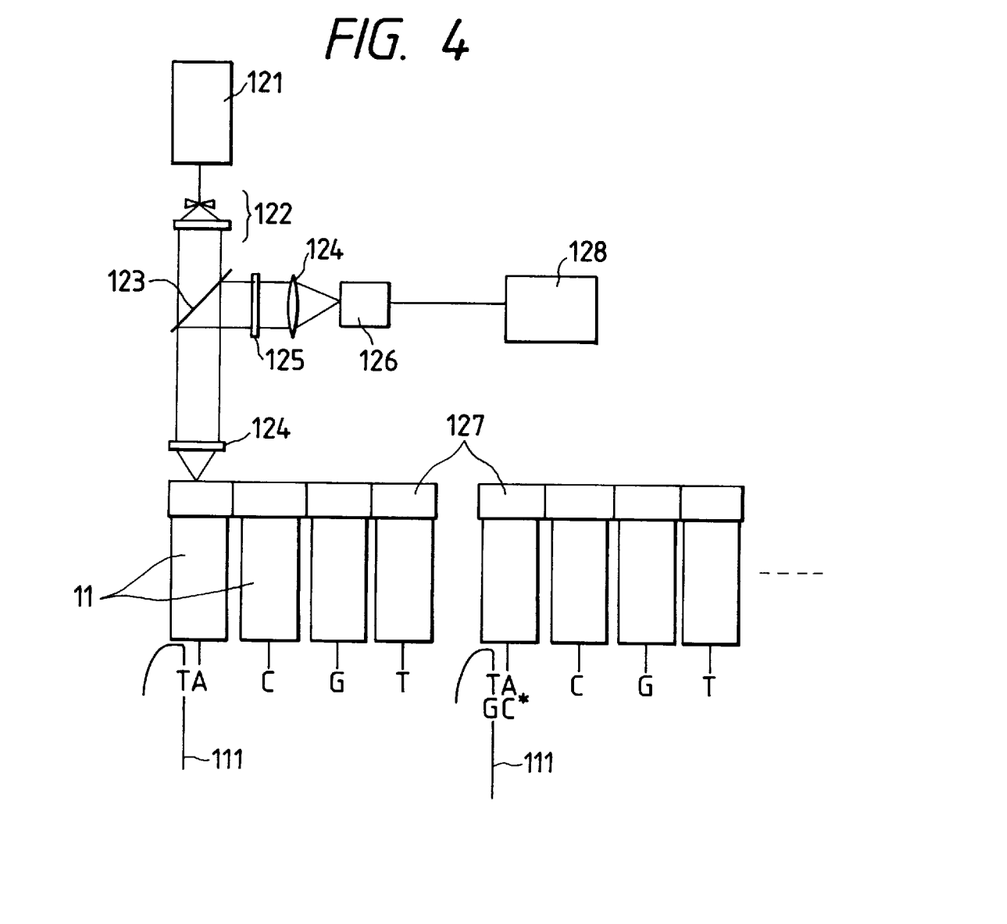
FIG. 4 is a schematic view of the detector for the analysis of the two bases at DNA fragment terminus.

By the method shown in FIG. 4, the sequence information up to the second base adjacent to the common sequence part of required DNA probes is brought about by measuring the presence or absence of the fluorescence on the surface of the glass rods. The method shown in FIG. 4 comprises expanding the laser beam from laser source 121 through beam expander 122, collimating the laser beam via lens 124 and introducing the laser beam through photocoupler 127. The laser beam projected onto the glass rod 11 reaches the top portion of the glass. Fluorescence is emitted if a fluorophore bonds to the DNA probe on the glass surface through the above reaction. Fluorescence progresses sequentially through the glass rod 11 and the photocoupler 127. Then, its direction is changed via dichroic mirror 123. The beam passing through filter 125 is introduced through the lens 124 into photodetector 126. By detecting the fluorescence from each glass rod and analyzing the data of detected signals with a computer, the terminal base sequence and a fluorescence emitting terminator can be identified. In other words, the terminal sequence of DNA fragments up to the second base can be identified by checking the type of a first base adjacent to the common sequence part and the type of the fluorescence labeled terminator introduced into the second base.

If fluorophors of different wavelengths are used for four types of fluorescence labeled terminators, i.e. dideoxyadenosine triphosphate ddATP*, dideoxycystein triphosphate ddCTP*, dideoxyguanosine triphosphate ddGTP* and dideoxytimine triphosphate ddTTP*, the reaction of a set of 4 slender rods instead of 4 rods will be sufficient. In such a case, the type of bases up to the second base adjacent to the common sequence part can be identified on the basis of the difference in fluorescence wavelength.

Figure 5:
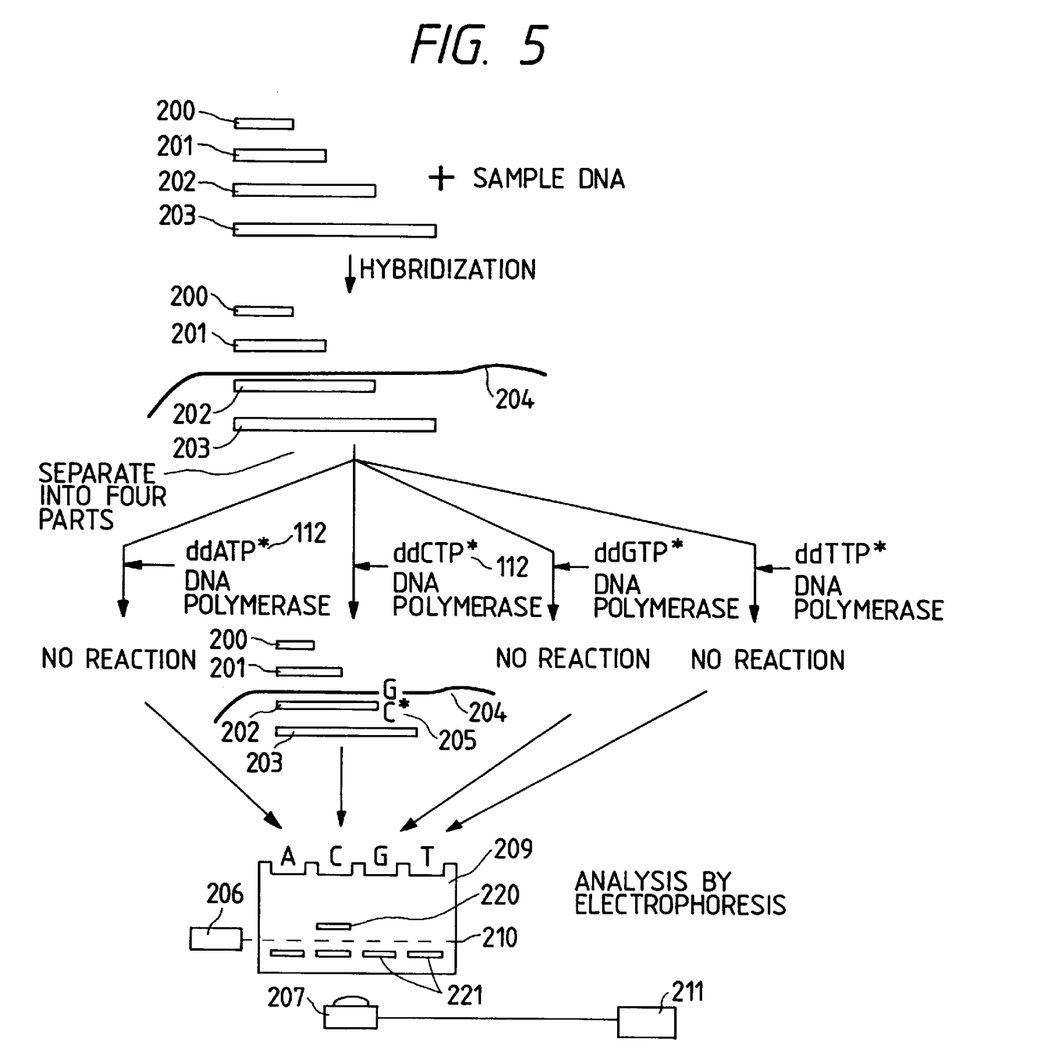
FIG. 5 is a view depicting another method for analyzing two bases at DNA fragment terminus.
Figure 6A:
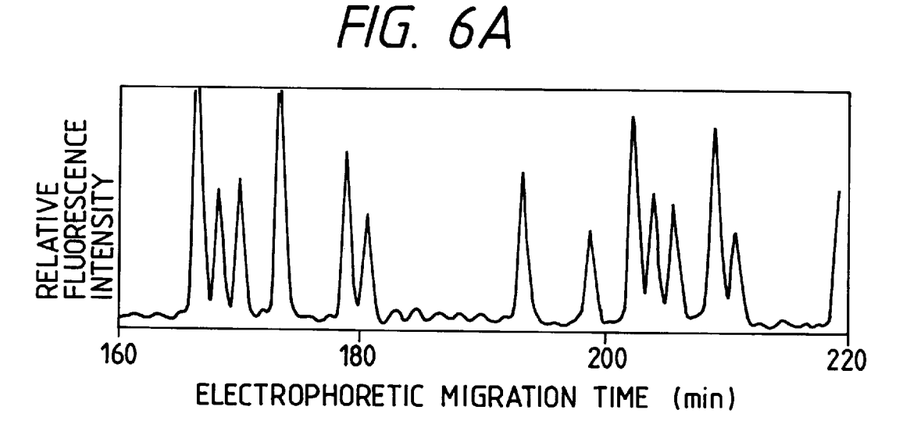
FIGS. 6A to 6E are views depicting one example of DNA sequencing results using the method of the present invention.
Figure 6B:
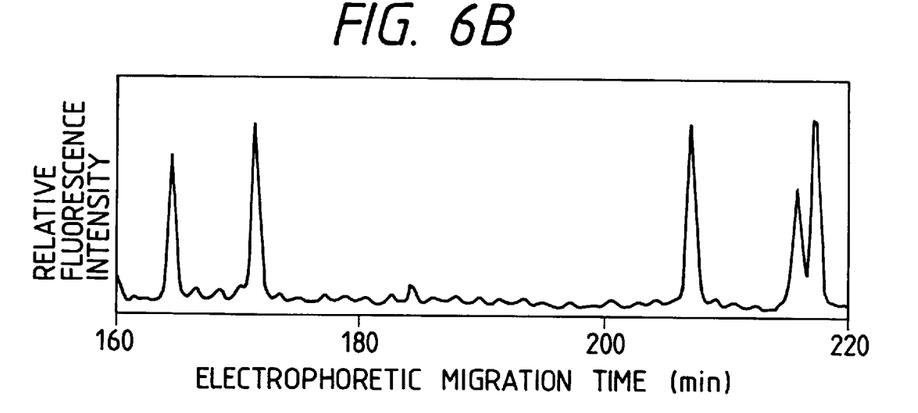
Figure 6C:
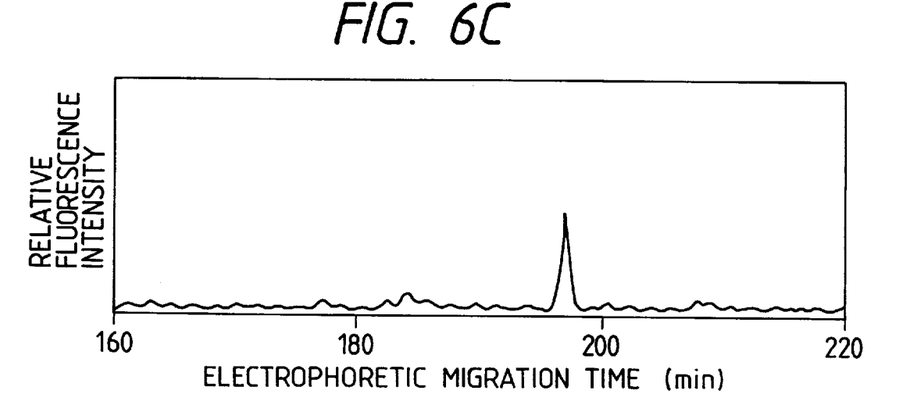
Figure 6D:
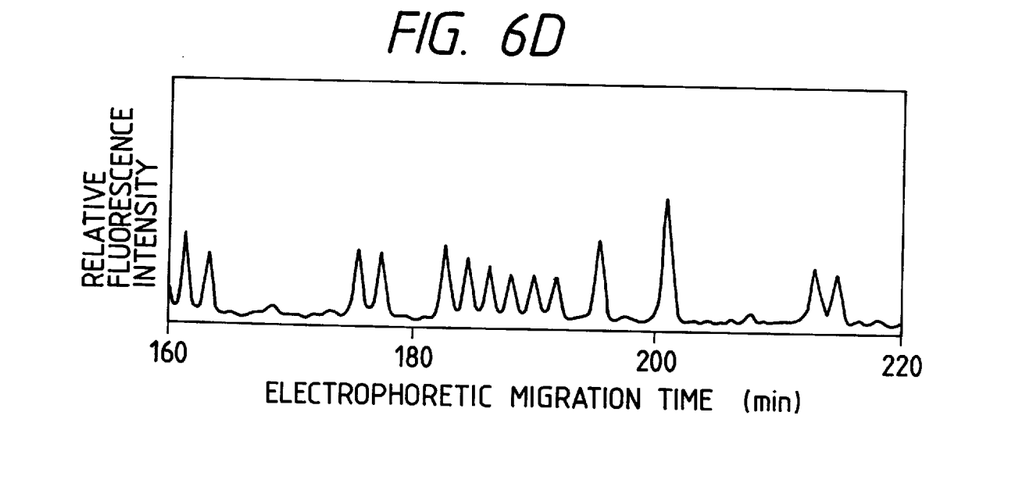
Figure 6E:
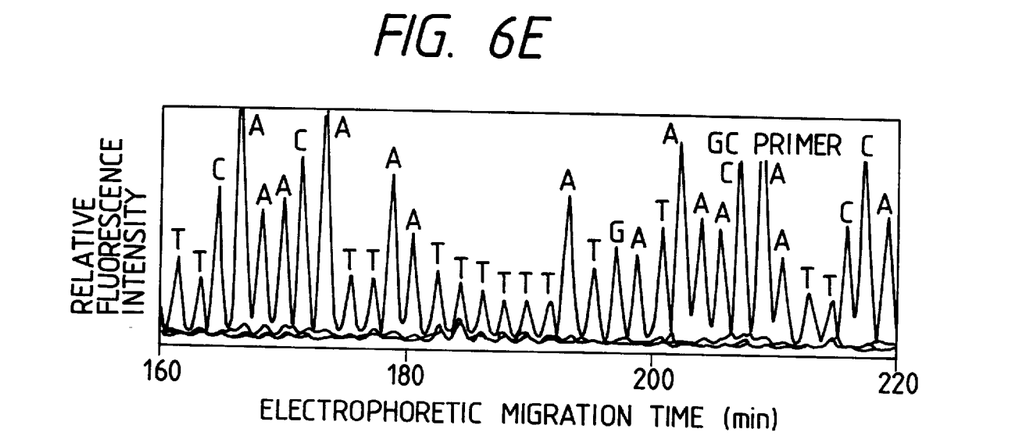

For another method to identify the 2-base sequence adjacent to the common sequence part of DNA fragments, DNA probes which have A, C, G and T as the bases adjacent to the common sequence part are prepared. The length of each DNA probe should be modified such as those of the DNA probes 200, 201, 202, and 203 as shown in FIG. 5, so that they can be identified individually by size separation by electrophoresis. After preparing a solution containing both sample DNA 204 and the aforementioned primers 200, 201, 202 and 203 for complementary strand extension, the solution is divided into four parts to check a second base species. To the individual divided solutions are added fluorescence labeled terminator 112 and DNA polymerase reactions are carried out. In such manner, fluorescence labeled terminator 205 bonds to the part of the second base adjacent to the common sequence part of the DNA probe. The reaction products are analyzed by electrophoresis for determining the terminal base species of the reaction products. From the electropherogram, the sequence information up to the second base adjacent to the common sequence part can be obtained. With an electrophoretic device for use in the electrophoretic analysis as shown in FIG. 5, laser beam 210 from laser source 206 irradiates electrophoretic gel 209 from the direction almost perpendicular to the direction of DNA fragment migration, to detect DNA band of probe 220 with an introduced fluorescence labeled terminator. The fluorescence from DNA bands is detected with photodetector 207.

So as to simplify the explanation of principle, FIGS. 3 to 5 illustrate a case where the sample DNA is single strand. As demonstrated in the present example, however, the information up to the second base adjacent to the common sequence part can be obtained even for a mixture containing a plurality of DNAs. In this example, it was found that eight types of probes were in complete matching with DNA fragments.

Another example is illustrated wherein by using a slender rod (probe chip) immobilized with DNA probes, DNA fragments produced by Hind III digestion of A phage DNA were separated for DNA sequencing. Fourteen types of DNA fragments were produced by digesting λ phage DNA with Hind III. As shown in FIG. 1, oligomer 2 of a known sequence is introduced into the terminus of the produced DNA fragments. As shown in FIG. 1, DNA probe 12, composed of known sequence part 13, which is complementary to the oligomer introduced into the DNA fragment terminus and a part of Hind III recognition sequence, and a sequence selecting part 14 having appropriate two bases adjacent to the 3' terminus of the known sequence part 13, is immobilized onto the separating rod. Because the number of combinations of appropriate two bases at the sequence selecting part amounts to 16, 16 types of DNA probes are necessary for separation DNA fragments. Thus, the number of slender rod types amounts to 16. According to the mentioned immobilization method, slender rods immobilized with the DNA probe are produced. In a solution containing 14 types of DNA fragments introduced with the oligomer of a known sequence is immersed a bundle of probe chips, produced by bundling individual slender rods immobilized with the 16 types of DNA fragments as prepared as described above. After thermal denaturing DNA fragments in the solution the DNA probes immobilized onto the slender rods react with the DNA fragments under hybridization conditions. Continuously, complementary strand extension progresses on the completely matched pairs. Furthermore, 30 cycles of such denaturing and hybridization followed by complementary strand extension are repeated. DNA fragments with 3' termini in incomplete hybridization as well as unreactive substances on the slender rods are washed off in aqueous solution at 70° to 80° C. By the method described above, DNA fragments in complete hybridization can be fractionated. By using a device as shown in FIG. 4, the slender rods on which the DNA fragments are in complete hybridization can be isolated. By heating to 96° C. the slender rods with the hybridized DNA fragments, the hybridized DNA fragments are released from the rods and fractionated. The sequences of the fractionated DNA fragments are determined by dideoxy terminator method using a fluorescence labeled primer. For example, FIG. 6 shows a part of the sequencing results of the DNA fragments isolated from the slender rods immobilizing a DNA probe where a sequence selecting part at 3' terminus is GC. For sequencing by the dideoxy terminator method, use is made as the primer of a DNA oligomer where a sequence selecting part at 3' terminus is GC as is the DNA probe immobilized on the slender rod. The sequencing reaction products by using four types of terminators (ddATP, ddCTP, ddGTP and ddTTP) are distinguished by different electrophoretic migration tracks for fluorescence detection. It is shown in FIGS. 6A, 6B, 6C and 6D, electropherogram of the sequencing reaction products produced by using the four types of terminators, ddATP, ddCTP, ddGTP and ddTTP. These electropherogram sets are shown simultaneously in FIG. 6E. In FIGS. 6A to 6D, the DNA bands corresponding to different bases are observed at different migration periods; the peak position does not overlap which indicates there is only one DNA fragment species to be analyzed in the sample solution. If the isolation of DNA fragments from a mixture is insufficient and there are plural of DNA fragments in a sample, a plurality of peaks (four peaks derived from A, C, G and T, at maximum) should be observed at the same peak positions. No overlapping of peak positions as shown in FIGS. 6A to 6D verifies that the isolation and fractionation of DNA fragments according to the present invention is satisfactory. The base species, therefore the sequence, are as shown in the figures. As has been described above, the sequence is obtained as shown in sequence No. 1, which corresponds to a partial sequence of λ phage DNA. As demonstrated here, the fractionation method in accordance with the present invention is advantageous in sequencing a plurality of DNA fragments directly from the mixed state thereof without cloning procedure.

In the above example, DNA fragments trapped on probe chips are used for analysis, but DNA probes extended on solid surface may be used for analysis as well. When a complementary strand extends in full length by using a DNA probe immobilized on the tip of a slender rod as a primer for complementary strand extension, the common sequence part should appear at 3' terminus of the extended probe (the oligomer bonds to both ends of a double strand DNA fragment through ligation), so that the analysis can be started from the 3' terminus of the extended strand by using a primer of a known sequence. Also, when a trapped DNA strand is too long for sequencing it at one step, the DNA is separated to be collected, prior to the cleavage with another restriction enzyme to digest the DNA into smaller fragments, which are then repeatedly subjected to the above procedure for sequencing.

In the above example, the probability of complementary strand by hybridization is increased by repeating hybridization followed by DNA strand extension and dehybridization of DNA probes to DNA fragments. When a free primer having the common sequence part is added to the solution, PCR (polymerase chain reaction) progress simultaneously to increase the DNA fragment copy number during separation. For the objective of such application, it is preferable from the respect of efficiency that the common sequence parts bonded to both termini of DNA fragments should be different from each other, so that an immobilized probe and a free primer have individually different common sequence parts, each part thereof being of a different sequence.

PCR amplification using DNA probes immobilized separately according to their sequences on a solid support along with a free primer, provides a novel means for separation and amplification of a mixture. The DNA hybridized to an immobilized probe which is extended by a polymerase reaction stays substantially around the position (cell) fraction immobilizing the probe which is extended to produce a complementary strand even at a higher temperature of about 95° C. which temperature is for thermally dissociating a double strand into single strands. Alternatively, the DNA and DNA probe pair without complementary strand extension is less stable and it is readily dehybridized into single strands during the process of temperature elevation. This pair forms double strand more slowly during the process of temperature decrease. Therefore, the probability for the DNA to hybridize to another DNA probe becomes large after the single stranded DNA moves into another position (cell) fraction remote from the position (cell) where first hybridization occurs, and while repeating the process, the probability of the DNA reaching to DNA probe for stable hybridization increases. Alternatively, when the single stranded DNA forms a double strand with a completely hybridizable DNA probe, complementary strand extension is initiated for increasing the stability; during the process of temperature increase, the dissociation of double strand occurs more lately, while during the process of temperature decrease, more speedy hybridization occurs. Therefore, large migration of DNA by diffusion does not occur. By presetting the annealing temperature at a high temperature, such phenomenon can be more readily promoted. By repeating such procedure, multiplication of DNA strand at individual positions (cells) can be done.

In the above example, various DNA probes are used after immobilization onto solid surface such as slender rods individually separable, but the material is not limited to glass rods herein used. Also, the surface of plate materials such as glass plate may be fractionated to immobilize individual DNA probes for fractionation.

(Example 2)

Example 2 is an example to use the fractionated DNA fragments as template of DNA sequencing. As in Example 1, DNA fragments are grouped and retained on the top of narrow of ribbon for extending complementary strand. At the 3' terminus of the extended complementary strand is located the same common sequence as that of the oligomer previously attached via ligation. By raising temperature, the double strand is thermally dissociated into single strands, and then, all the ribbons are transferred into a vessel containing a reaction solution for DNA sequencing. As a primer, a complementary sequence to the common sequence at the 3' terminus is used. It is convenient to use the terminator ddNTP (dideoxy nucleotide triphosphate) labeled with different fluorophors depending on the base type. When a fluorescence labeled primer is used, four DNA extended strands immobilized on the strips of ribbon should be prepared to synthesize a fragment family with different base types for sequencing. After the termination of sequencing reaction, fragments of various lengths synthesized by using DNA polymerase reaction with a common primer are retained on the 3' terminus of the extended DNA of which the 5' terminus is immobilized on the top of the ribbon. Placing the ribbon onto the upper top of a gel plate, heating the ribbon for releasing the fragments produced by sequencing reaction for gel electrophoresis to identify the fragment length, the sequence is determined. The strips of ribbon are placed at different positions depending on the probe type, and the DNA fragments dissociated therefrom are separated by electrophoresis.

Sequence Table

Sequence No.: 1

Sequence length: 34

Sequence type: Nucleic Acid

Chain number: Double Strand

Sequence type: Bacterial phage DNA fragment

Sequence: TTCAAACATT AATTTTTTAT GATAAA-
CAAT TCCA, SEQ ID NO: 1

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 34 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TTCAAACATT AATTTTTAT GATAAACAAT TCCA                    3 4

What is claimed is:

1. A separation and fractionation method for restriction enzyme digested DNA fragments, comprising the steps of:

i) mixing an oligonucleotide having a known sequence with the digested DNA fragments and ligating the oligonucleotide to at least one of a 3' terminus and 5' terminus of each of the digested DNA fragments, and preparing a single probe chip or a set of probe chips by immobilizing a DNA probe to a solid surface by its 5' terminus, said DNA probe having a known sequence part and a selective sequence part, said known sequence part being complementary to the sequence of the oligonucleotide and at least a part of a restriction enzyme recognition sequence on the digested DNA fragments, and said selective sequence part is composed of one to six bases and is any possible combination of said one to six bases; and wherein said DNA probe selects by hybridization thereto, one DNA fragment from a mixture of the restriction enzyme digested DNA fragments, wherein the single probe chip immobilizes the DNA probe having the selective sequence part composed of one to six bases, or wherein each probe chip of the set of probe chips respectively immobilizes the DNA probe having a different selective sequence part composed of one to six bases;

ii) dipping the single probe chip or the set of probe chips in a solution containing the digested DNA fragments ligated to the oligonucleotide;

iii) hybridizing the digested DNA fragments ligated to the oligonucleotide to the DNA probe;

iv) extending a resulting hybridized DNA probe by a complementary strand extension reaction in the solution to create an extended DNA probe; and v) separating and fractionating an extended DNA probe immobilized on the single probe chip or any one of the probe chip of the set of probe chips, wherein the DNA fragments which do not sufficiently hybridize to the DNA probe to permit the complementary strand extension reaction are separated from the single probe chip or the set of probe chips.

2. The method according to claim 1, wherein the probe chip or each of the probe chips of the set of probe chips is a slender rod, wire, sheet or ribbon.

3. The method according to claim 1, wherein the probe chip is a slender rod made of glass.

4. The method according to claim 1, further comprising the steps of:

ivA) raising the temperature of the solution resulting from step iv), and removing the DNA fragments hybridized with a DNA probe not extended by the complementary strand extension reaction, while leaving the extended DNA probe hybridized to the digested DNA fragments ligated to the oligonucleotide, wherein the steps of iv) and ivA) are repeated at least once.

5. The method according to claim 1, wherein the set of probe chips are simultaneously dipped in the solution containing the digested DNA fragments ligated to the oligonucleotide.

6. The method according to claim 1, wherein a free oligomer having a sequence identical to said known sequence part is added to the solution in step iv), and a polymerase chain reaction progresses simultaneously to increase the number of copies of the digested DNA fragments ligated to the oligonucleotide by raising and lowering the temperature of the solution to effect the polymerase chain reaction.

7. The method according to claim 9, wherein at 3' and 5' termini of each of the digested DNA fragments, oligonucleotides having different sequences composed of the known sequence part and at least the part of the enzyme recognition sequence are ligated.

8. The method according to claim 1, wherein the oligonucleotide is tagged with a fluorophore.

9. A DNA sequencing method for determining a DNA sequence of the DNA fragment separated and fractionated according to claim 1, wherein the DNA sequence of the DNA fragment is determined by electrophoresis.

10. A separation and fractionation method for restriction enzyme digested DNA fragments comprising the steps of:

i) mixing an oligonucleotide having a known sequence with the digested DNA fragments and ligating the oligonucleotide to a 3' terminus of the digested DNA fragments, and preparing a solid probe chip by immobilizing a DNA probe at its 5' terminus to the solid probe chip, said DNA probe having a known sequence part and a selective sequence part, said known sequence part being complementary to the sequence of the oligonucleotide and at least a part of an enzyme recognition sequence of said restriction enzyme on said DNA fragments, and said selective sequence part is composed of one to six bases, and is any possible combination of said one to six bases; and wherein said DNA probe selects by hybridization thereto, one DNA fragment from a mixture of the restriction enzyme digested DNA fragments, wherein the solid probe chip immobilizes the DNA probe having a different selective sequence part, on different positions on a surface of the solid probe chip respectively;

ii) dipping the solid probe chip in a solution containing the digested DNA fragments ligated to the oligonucleotide;

iii) hybridizing the digested DNA fragments ligated to the oligonucleotide to the DNA probe, iv) extending a resulting hybridized DNA probe by a complementary strand extension reaction in the solution; and v) separating and fractionating DNA fragments hybridized to extended DNA probes immobilized on the surface of the solid probe chip wherein the DNA fragments which do not sufficiently hybridize to the DNA probe to permit the complementary strand extension reaction are separated from the solid probe chip.

11. The method according to claim 10, further comprising the steps of:

ivA) raising the temperature of the solution resulting from step iv), and removing the DNA fragments hybridized with the DNA probe not extended by the complementary strand extension reaction, while leaving the extended DNA probe hybridized to the digested DNA fragments ligated to the oligonucleotide, wherein the steps of iv) and ivA) are repeated at least once.

12. The method according to claim 10, wherein a free oligomer having a sequence identical to said known sequence part is added to the solution in step iv), and a polymerase chain reaction progresses simultaneously to increase the number of copies of the digested DNA fragments ligated to the oligonucleotide by raising and lowering the temperature of the solution to effect the polymerase chain reaction.

13. The method according to claim 10, wherein at 3' and 5' termini of each of the digested DNA fragments, oligonucleotides having different sequences composed of the known sequence part and at least the part of the enzyme recognition sequence of the restriction enzyme are ligated.

14. The method according to claim 13, wherein an oligonucleotide is tagged with a fluorophore.

15. A DNA sequencing method for determining a DNA sequence of the DNA fragment separated and fractionated according to claim 10, wherein the DNA sequence of the DNA fragment is determined by electrophoresis.

16. A separation and fractionation method for restriction enzyme digested DNA fragments comprising the steps of:

i) mixing an oligonucleotide tagged with a fluorophore and having a known sequence with the digested DNA fragments and ligating the oligonucleotide to at least one of a 3' terminus and a 5' terminus of each of the digested DNA fragments, and preparing a plurality of probe chips by immobilizing a DNA probe at its 5' terminus to the probe chips, said DNA probe having a known sequence part and a selective sequence part, said known sequence part being complementary to the sequence of the oligonucleotide and at least a part of an enzyme recognition sequence of said restriction enzyme on said DNA fragments, and said selective sequence part is composed of one to six bases, and is any possible combination of said one to six bases; and wherein said DNA probe selects by hybridization thereto, one DNA fragment from a mixture of the digested DNA fragments, wherein each of the plurality of probe chips respectively immobilizes the DNA probe having a different selective sequence part composed of the combinations of one to six bases;

ii) dipping the plurality of probe chips in a solution containing the digested DNA fragments ligated to the oligonucleotide;

iii) hybridizing the digested DNA fragments ligated to the oligonucleotide to the DNA probe;

iv) extending a resulting hybridized DNA probe by a complementary strand extension reaction in the solution; and v) washing off DNA probes not extended by the complementary strand extension reaction from each of the probe chips at a first temperature in the solution, and releasing from the probe chips an extended DNA probe by the complementary strand extension reaction from the probe chips at a second temperature higher than the first temperature in a solution for separation and fractionation of the digested DNA fragments ligated to the oligonucleotide;

wherein each of said probe chips is a slender rod, wire, sheet or ribbon.

17. The method according to claim 16, wherein the plurality of probe chips are simultaneously dipped in the solution containing the digested DNA fragments ligated to the oligonucleotide.

18. The method according to claim 16, wherein the probe chips are slender rods made of glass.

19. A DNA sequencing method for determining a DNA sequence of the DNA fragment separated and fractionated according to claim 16, wherein the DNA sequence of the DNA fragment is determined by electrophoresis.

20. A distinguishing method for enzyme, digested DNA fragments comprising the steps of:

i) mixing an oligonucleotide having a known sequence with the digested DNA fragments and ligating the oligonucleotide to a 3' terminus of the DNA fragments, and preparing a DNA probe having a known sequence part and a selective sequence part, said known sequence part being complementary to the sequence of the oligonucleotide and at least a part of an enzyme recognition sequence of the DNA fragments, and said selective sequence part is composed of one to six bases, and is any possible combination of said one to six bases; and wherein said DNA probe selects by hybridization thereto, a digested DNA fragment from a mixture of the digested DNA fragments;

ii) hybridizing the DNA fragments ligated to the oligonucleotide to the DNA probe in a solution;

iii) extending the hybridized DNA probe by a complementary strand extension reaction; and iv) distinguishing DNA fragments hybridized with the DNAs probes not extended by the complementary strand extension reaction from the DNA fragments hybridized with the DNA probe extended by the complementary strand extension reaction.

21. The method according to claim 20, wherein the DNA probe is immobilized on a probe chip or a set of probe chips separately with each species separated by their selective sequences and the probe chip is a slender rod, wire, sheet or ribbon.

22. The separation and fractionation method according to claim 21, wherein the probe chip is a slender rod made of glass.

23. The method according to claim 20, wherein the DNA probe having the different selective sequence part immobilized at a 5' terminus of the DNA probe onto a solid probe chip at different surface positions on the solid probe chip.

24. The method according to claim 20, wherein a free oligomer having a sequence composed of the known sequence part, complementary to the sequence of the oligonucleotide and at least the part of the enzyme recognition sequence, is added to the solution in step of ii), and the polymerase chain reaction progresses simultaneously to increase the number of copies of the DNA fragments ligated to the oligonucleotide by raising and lowering temperature.

25. The method according to claim 20, wherein at the 3' and 5' terminus of each of the digested DNA fragments, oligonucleotides having different sequences composed of the known sequence part complementary to the sequence of the oligonucleotide and at least the part of the enzyme recognition sequence are ligated respectively.

26. The method according to claim 20, wherein the oligonucleotide is tagged by a fluorophore.

27. The method according to claim 20, wherein the enzyme is a restriction enzyme.

28. A distinguishing method for enzyme digested DNA fragments according to claim 20, wherein the DNA sequences of the DNA fragments are determined by generating shorter DNA fragments of said DNA fragment or shorter DNA fragments complementary to said DNA fragment and separating said shorter DNA fragments by electrophoresis.

29. A separation and fractionation method for enzyme digested DNA fragments comprising the steps of:

i) hybridizing said DNA fragments to a set of DNA probes each probe having a sequence common to every probe and a selective sequence composed of one to six bases at a 3' terminus of the DNA probes;

ii) extending the DNA probes hybridized to the DNA fragments by a complementary strand extension reaction to make an extended DNA probe; and iii) separating and fractioning the DNA fragments hybridized to the extended DNA probe from the DNA fragments hybridized to the DNA probes not extended using differences in hybridization stability.

30. A separation and fractionation method for enzyme digested DNA fragments according to claim 29, wherein the DNA sequences of the DNA fragments are determined by generating shorter DNA fragments of said DNA fragment or shorter DNA fragment copies complementary to said DNA fragment and separating said shorter DNA fragments by electrophoresis.

31. A sequence distinguishing method for enzymatically digested DNA fragments comprising the steps of:

i) hybridizing said DNA fragments to a set of DNA probes, each probe having a sequence common to all of the DNA probes and a selective sequence part composed of two bases at a 3' terminus of the DNA probes, each probe differing according to differences in the two bases at the 3' terminus of the DNA probe, the two bases being adjacent to an enzyme recognition site;

ii) extending the hybridized DNA probes by a complementary strand extension reaction to form completely matched base pairs of said DNA fragments; and iii) distinguishing an extended DNA probe from non-extended DNA probes using differences in hybridization stability.

32. A DNA sequencing method for determining DNA sequences of the DNA fragments distinguished according to claim 31, wherein the DNA sequences of the DNA fragments are determined by generating shorter DNA fragments of said DNA fragment or shorter DNA fragment copies complementary to said DNA fragment and separating said shorter DNA fragments by electrophoresis.

33. A classification method for restriction enzyme digested DNA fragments comprising the steps of:

classifying DNA fragments in a mixture according to their terminal one to six base sequences adjacent to the restriction enzyme recognition sequence of the DNA fragments, by hybridizing said DNA fragments to a set of DNA probes followed by a complementary strand extension reaction to extend the DNA probes, and classifying the DNA fragments by electrophoresis, wherein said set of DNA probes has a sequence common to all DNA probes and a selective sequence part composed of one to six bases at a 3' terminus of the DNA probe.

34. The method according to claim 1, wherein the probe chip is transparent.

* * * * *